US010472485B2

(12) United States Patent
Lee et al.

(10) Patent No.: US 10,472,485 B2
(45) Date of Patent: Nov. 12, 2019

(54) COMPOSITE POWDER IN WHICH POROUS POLYMER IS IMPREGNATED WITH SCORIA POWDER PARTICLES, COSMETIC COMPOSITION CONTAINING SAME, AND PROCESS FOR PRODUCING SAME (71) Applicant: AMOREPACIFIC CORPORATION, Seoul (KR)

(72) Inventors: Hyun Suk Lee, Yongin-si (KR); Dong-Hyun Paik, Siheung-si (KR); Jin Seob Shin, Yongin-si (KR); Mi-Suk Yang, Yongin-si (KR); Sung-Wook Choi, Bucheon-si (KR); Yong Jin Kim, Yongin-si (KR); John Hwan Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/764,935

(22) PCT Filed: Sep. 26, 2016

(86) PCT No.: PCT/KR2016/010786
§ 371 (c)(1),
(2) Date: Mar. 30, 2018

(87) PCT Pub. No.: WO2017/057886
PCT Pub. Date: Apr. 6, 2017

(65) Prior Publication Data
US 2019/0040224 A1 Feb. 7, 2019

(30) Foreign Application Priority Data

Sep. 30, 2015 (KR) .................. 10-2015-0137327
Sep. 23, 2016 (KR) .................. 10-2016-0122454

(51) Int. Cl.
C08J 9/40 (2006.01)
A61Q 19/00 (2006.01)
(Continued)

(52) U.S. Cl.
CPC ................. C08J 9/40 (2013.01); A61K 8/025 (2013.01); A61K 8/0279 (2013.01);
(Continued)

(58) Field of Classification Search
None
See application file for complete search history.

(56) References Cited

U.S. PATENT DOCUMENTS 4,595,364 A * 6/1986 Kusano ................. A61C 13/04
433/185
2014/0235634 A1 8/2014 Ong et al.

FOREIGN PATENT DOCUMENTS

FR 2969490 A1 6/2012
JP 2009-501209 A 1/2009
(Continued)

OTHER PUBLICATIONS

Sugimoto et al., "Cations Inhibit Specifically Type I 5a-Reductase Found in Human Skin", The Journal of Investigative Dermatology, 1995, vol. 104, pp. 775-778.
(Continued)

Primary Examiner — Robert A Wax
Assistant Examiner — Melissa S Mercier
(74) Attorney, Agent, or Firm — Lucas & Mercanti, LLP (57) ABSTRACT The present invention relates to a composite powder of scoria powder and a porous polymer. More particularly, the present invention relates to a composite powder (scoria sphere) in which the surface and the inside of a porous polymer are uniformly impregnated with scoria powder particles prepared by spraying in one-step a dispersion in
(Continued)

which scoria powder is dispersed in a solution in which a polymer is dissolved; a cosmetic composition containing the same; and a process for producing the same. When the scoria impregnated powder, of the present invention, in which the porous polymer is uniformly impregnated with the scoria powder particles, is formulated as a cosmetic composition, the porous polymer supplements the sebum absorption performance of the scoria miniaturized in a micro size, and thus the sebum absorption power is greatly improved.

10 Claims, 5 Drawing Sheets

(51) Int. Cl.
| | | |
|---|---|---|
| | *A61K 8/26* | (2006.01) |
| | *A61K 8/31* | (2006.01) |
| | *A61K 8/34* | (2006.01) |
| | *A61Q 1/00* | (2006.01) |
| | *A61Q 5/00* | (2006.01) |
| | *A61K 8/81* | (2006.01) |
| | *A61K 8/02* | (2006.01) |
| | *C08J 3/12* | (2006.01) |
| | *C08K 7/26* | (2006.01) |
| | *C08J 3/21* | (2006.01) |

(52) U.S. Cl.
CPC .............. *A61K 8/0287* (2013.01); *A61K 8/26* (2013.01); *A61K 8/315* (2013.01); *A61K 8/34* (2013.01); *A61K 8/8152* (2013.01); *A61Q 1/00* (2013.01); *A61Q 5/00* (2013.01); *A61Q 19/00* (2013.01); *C08J 3/12* (2013.01); *C08J 3/122* (2013.01); *C08J 3/212* (2013.01); *C08K 7/26* (2013.01); *A61K 8/022* (2013.01); *A61K 2800/412* (2013.01); *A61K 2800/56* (2013.01); *A61K 2800/61* (2013.01); *A61K 2800/654* (2013.01); *C08J 2325/06* (2013.01); *C08J 2333/12* (2013.01); *C08J 2339/06* (2013.01); *C08J 2367/04* (2013.01); *C08J 2371/02* (2013.01); *C08J 2383/04* (2013.01); *C08K 2201/005* (2013.01)

(56) References Cited

FOREIGN PATENT DOCUMENTS

| | | | | |
|---|---|---|---|---|
| KR | 10-2010-0065832 A | | 6/2010 | |
| KR | 2010065832 | * | 6/2010 | |
| KR | 20100062832 A | * | 6/2010 | |
| KR | 10-2011-0062708 A | | 6/2011 | |
| KR | 20110062708 A | * | 6/2011 | .......... A61K 8/0279 |
| KR | 10-2013-0114013 A | | 10/2013 | |
| KR | 10-1415996 B1 | | 7/2014 | |
| KR | 10-2014-0101593 A | | 8/2014 | |
| WO | 2007-020536 A2 | | 2/2007 | |

OTHER PUBLICATIONS

Bruchovsky et al., The Conversion of Testosterone to 5α-Androstan 17 β-ol-3-one by Rat Prostate in Vivo and in Vitro, The Journal of Biological Chemistry, 1968, vol. 243. No. 8, pp. 2012-2021.
Thiboutot et al., "Activity of the Type 1 5α-Reductase Exhibits Regional Differences in Isolated Sebaceous Glands and Whole Skin", The Journal of Investigative Dermatology, 1995, vol. 105, pp. 209-214.
International Search Report for International Application No. PCT/KR2016/010786. (2 Pages) (dated Dec. 27, 2016).
The extended European search report, Application No. 16852032.8, dated Sep. 12, 2018.

* cited by examiner

COMPOSITE POWDER IN WHICH POROUS POLYMER IS IMPREGNATED WITH SCORIA POWDER PARTICLES, COSMETIC COMPOSITION CONTAINING SAME, AND PROCESS FOR PRODUCING SAME

CROSS-REFERENCE TO RELATED APPLICATIONS

This application is a 371 of PCT/KR2016/010786, filed Sep. 26, 2016 which claims the benefit of Korean Patent Application No. 10-2015-0137327, filed Sep. 30, 2015 and Korean Patent Application No. 10-2016-0122454, filed Sep. 23, 2016, the contents of each of which are incorporated herein by reference.

TECHNICAL FIELD

The present invention relates to a composite powder of scoria powder and a porous polymer. More particularly, the present invention relates to a composite powder (scoria sphere) in which the surface and the inside of a porous polymer are uniformly impregnated with scoria powder particles wherein the scoria powder particles are prepared by spraying in one-step a dispersion formed by dispersing scoria powder in a solution in which a polymer is dissolved, a cosmetic composition containing the same; and a method for preparing the same.

BACKGROUND ART

Scoria (scientific name) is known as a kind of natural ceramics which are pyroclastic deposits made by burning clay at high temperatures due to volcanic activity. When a volcano erupts, the scoria is formed by the hardening of the first erupted lava. At this time, the lava mixed with the gas is ejected first, and the scoria with a porous structure containing numerous fine holes is created in this process.

In Korea, the scoria is found in Jeju Island, and it is called Song-ee or Song-ee stone according to the dialect of Jeju Island. The physical property of scoria is weak alkaline with pH of approximately 7.2 to 7.8 and is porous, and the scoria exhibits colors such as reddish brown, yellowish brown, black and gray depending on the mineral constituents commonly contained.

Meanwhile, 5α-reductase, which is present in male hormone reactive tissues such as sebaceous glands, hair follicles, prostate, and epididymis, is an enzyme involved in the reduction of testosterone, which is one of the male hormones, to dihydrotestosterone (DHT). It is known that testosterone is involved in the increase of skeletal muscle, spermatogenesis, and the like, and dihydrotestosterone is involved in acne, increased sebum, prostatic hyperplasia and the like in the relevant tissues (Diane et al; J. Invest Dermatol. 775-778, 1995. Bruchovsky, N et al; J.B.C. 243, 2112-2121, 1968). Additionally, in the sebum gland of the skin, testosterone is converted to dihydrotestosterone by 5α-reductase and binds to a receptor protein in the cytoplasm to enter the nucleus and activate sebum gland cells and thus promote differentiation, thereby hypersecreting sebum in the sebum gland (Diane et al; J. Invest Dermatol. 105; 209-214).

In this regard, the present applicants have disclosed in Korean Patent Publication No. 1415996 that the scoria effectively inhibits the activity of 5α-reductase and thus has effects related to sebum control, the contraction of hair pouch and skin troubles.

In addition, it has been known that since the scoria contains a large amount of natural minerals and its own far-infrared emissivity is high, it has physical properties such as superior antibacterial activity and excellent deodorizing property. Also, it is a trend that since the scoria contains a large amount of natural minerals, the utility of scoria is increasing as a variety of cosmetic materials for skin moisturizing, the contraction of hair pouch, washing, antibacterial, and the like The scoria is a porous material with a large particle size, which is a kind of pyroclastic deposits, but, the scoria is usually crushed into small particles and added when used as a cosmetic ingredient. However, if the scoria is crushed into micro size for cosmetic material, the porous structure is destroyed and the sebum absorption performance is lost. Also, due to the crystalline structure, because a disadvantage of the rough feeling of use cannot be avoided, there is a need for a porous composite powder structure with excellent sebum absorption performance without the scoria powder being directly exposed to the skin.

Prior Art Literature

Korean Patent No. 1415996, "Cosmetic composition containing scoria."

DISCLOSURE

Technical Problem

In order to solve the above problems, although a method of coating the surface of the scoria powder with polymer materials can be used, it cannot solve the disadvantage that the sebum causes the particles to aggregate and the dispersibility is reduced. In addition, although the scoria powder and the porous raw materials can be used individually in the formulation, there is a problem that the scoria powder of coarse crystalline structure is directly exposed to the skin and thus the feeling of use is greatly reduced. In addition, although there is an emulsion polymerization method as a technology to make the porous polymer, there are no precedent successes in impregnating the inorganic powder while making porous polymer, due to technical limitations, and the removal of the surfactant is not easy even if it can be prepared, and thus there is a disadvantage that the control of the physical properties of the surface is difficult.

Technical Solution

In order to solve such problems, the present invention discloses a scoria impregnated powder (scoria sphere) prepared by dispersing the scoria powder in a polymer-dissolved solution and then spraying the dispersion in one-step of spray drying or electro-spraying to uniformly impregnate the scoria powder particles into a porous polymer; a cosmetic composition containing the same; and a method for preparing the same. The particles of the scoria powder have a particle size of 5 to 20 μm and may be impregnated in an amount of 10 to 90% by weight, preferably 50 to 90% by weight, based on the total weight of the composite powder. The porous polymer is preferably at least one selected from the group consisting of poly-(methyl methacrylate) [PMMA], poly-(vinyl pyrrolidone) [PVP], poly-(caprolactone) [PCL], poly-(L-lactic acid) [PLLA], poly-(ethylene oxide) [PEO], poly-(propylene oxide) [PPO], poly-(dimethyl siloxane) [PDMS], poly-(lactic-co-glycolic acid)

[PLGA], polystyrene [PS] and a copolymer thereof, and its specific volume is preferably 0.5 to 5 cm$^3$/g.

Advantageous Effects

If the scoria impregnated powder (scoria sphere) of the present invention prepared by uniformly impregnating the scoria powder particles with a porous polymer is formulated as a cosmetic composition, the sebum absorption performance of the scoria minified into micro size is complemented by the porous polymer, and thus the sebum absorption power is greatly improved.

In addition, when a spray drying or electro-spraying process is introduced to produce the scoria impregnated powder (scoria sphere) of the present invention, it can be uniformly impregnated on the surface and inside the porous polymer of the sphere in one step, while excluding the use of emulsifying agents that are irritating to the skin.

Also, by impregnating the coarse and crystalline scoria powder into the inside of the porous polymer of the sphere, there are effects of improving the applicability, spreadability, softness and eliminating the aggregation phenomenon.

BEST MODE

The present invention relates to a composite powder of a scoria powder and a porous polymer. More particularly, the present invention relates to a composite powder (hereinafter referred to scoria impregnated powder or scoria sphere) prepared by dispersing the scoria powder in a polymer-dissolved solution and then spraying the dispersion in one-step of spray drying or electro-spraying to uniformly impregnate the scoria powder particles on the surface and inside the porous polymer; a cosmetic composition containing the same; and a method for preparing the same. The term "impregnation" as used herein refers to a state in which other powder particles are uniformly dispersed and penetrated through the interior of the matrix of powder particles and differs from the conventional form in which the surfaces of the powder particles are coated with other powder particles or carried between the pores of the surface of the powder. Hereinafter, the present invention will be described in detail.

Scoria Powder

The scoria used as an effective ingredient in the present invention is a kind of volcanic ash existing only in Jeju Island, Korea, and it is known that the scoria was erupted during the formation of a parasitic volcano (oreum) throughout Jeju Island. The reserve of the scoria in Jeju Island are estimated to be about 20,000,000,000 m$^3$, which is a nearly infinite resource. The scoria is a natural material that has the ability to combat *Escherichia coli* with a far infrared emissivity of 92% to 93%, a deodorization rate of 97% and an antimicrobial activity of 99.9% against fungi in its natural state.

The scoria of the present invention can be obtained by a conventional method in the art, and the production method thereof is not particularly limited. Specifically, for example, the scoria powder can be obtained by pulverizing the scoria collected in an area uncontaminated by pesticides or the like into particles of various sizes depending on the usage to remove impurities and then dry-heat sterilizing at a temperature of 150° C. or higher.

However, the particles of the scoria powder which can be used as the cosmetic composition in the present invention are preferably processed to have an average particle diameter of 0.1 to 2 µm. This is because if the diameter is more than 2 µm, the effect of scoria powder is insufficient, and if the diameter is less than 0.1 µm, the surface of the scoria impregnated powder (scoria sphere) of the sphere becomes rough and the feeling of use is lowered when applied to the skin.

Porous Polymer

The porous polymer impregnated with the scoria powder particles in the present invention is a sphere powder phase with oil absorption and sebum absorption.

In one embodiment, poly-(methyl methacrylate) [PMMA] was applied as the porous polymer, but it may be selected from the group consisting of poly-(vinyl pyrrolidone) [PVP], poly-(caprolactone) [PCL], poly-(L-lactic acid) [PLLA], poly-(ethylene oxide) [PEO], poly-(propylene oxide) [PPO], poly-(dimethyl siloxane) [PDMS], poly-(lactic-co-glycolic acid) [PLGA], polystyrene [PS] and a copolymer thereof, among the others, but it is not limited thereto.

Since the shape of the particles in the porous polymer is a sphere, it is easy to formulate in the preparation of various cosmetic formulations, and since the particles of the sphere phase are rolled on the skin, the feeling of use such as spreadability when applying to the skin is excellent. Due to the effect of preventing shine of the skin by light scattering, which is the characteristic of the surface of the sphere, and the enhancement of makeup persistence, the porous polymers are commonly used in foundation cosmetics for sebum control and in make-up products for skin tone correction.

Scoria Impregnated Powder (Scoria Sphere)

The scoria impregnated powder (scoria sphere) of the present invention, that is, a composite powder prepared by uniformly impregnating the scoria powder particles on the surface and inside the porous polymer of the sphere, has preferably a particle diameter of 5 to 20 µm. This particle size is related to the oil absorption volume and feeling of use. If the particle size is less than 5 µm, there is a possibility that the stability of the cosmetic material deteriorates due to agglomeration of the particles, and if the particle size exceeds 20 µm, the unpleasant feeling of use can be felt by the particles when added to cosmetic compositions and applied to the skin.

The scoria powder in the scoria impregnated powder may be impregnated in an amount of 10 to 90% by weight based on the total weight of the scoria impregnated powder, but the impregnation of 50 to 90% by weight is most preferable for the effect by the scoria powder and the feeling of use when applied to the skin.

In addition, the scoria impregnated powder can be controlled in its pore characteristics depending on the conditions of the manufacturing process. The controllable pore characteristics include average pore size, porosity, and total area of pore. Specifically, the average pore size may be 15 to 800 nm, more preferably 250 to 600 nm, and the porosity may be 40 to 85%, and more preferably 50 to 75%. Also, the total area of the pores may be from 1 to 100 m$^2$/g, and more preferably from 5 to 80 m$^2$/g.

This scoria impregnated powder with these characteristics can induce the increase of oil absorption volume due to its pore size and porosity. The oil absorption volume can be explained by the intrusion volume of mercury as described below. The intrusion volume of mercury of the scoria impregnated powder according to the present invention is measured in the range of 0.5 to 5 cm$^3$/g, which can be regarded as an oil absorption volume with high confidence level.

The conventional porous polymers have a relatively large specific surface area due to a single-sized mesoporous structure but have a low average pore size and low porosity, whereas the scoria impregnated powder of the present invention has a pore channel due to the structure of multi-porous (micro+meso+macro), and thus is more advantageous for oil absorption by capillary phenomenon.

The present invention makes it possible to uniformly impregnate the scoria powder on the surface and inside the porous polymer by spraying a polymer dispersion in one-step of spray drying or electro-spraying to prepare a porous scoria impregnated powder wherein the polymer dispersion is produced by dispersing the scoria powder in the polymer solution. At this time, it is preferable to exclude the emulsifier for maximizing the oil absorption capacity and realizing a super water repellent property. The detailed processes of spray drying and electro-spraying are not particularly limited in the present invention but follow a known method. The composite powder thus prepared can be freeze-dried to remove the solvent sufficiently to maintain the particle shape of the sphere.

However, the solvent of the polymer solution may preferably be a solvent formed by mixing poly-(methyl methacrylate) (PMMA) with dichloromethane (DCM) and hexanol. The mixing ratio (weight ratio) of dichloromethane (DCM) and hexanol can be selected from 9:1 to 7:3. Since hexanol plays a role in forming a porous polymer pore, if the proportion of hexanol is less than 10 wt. % of the total solvent, the pore size is too small, and if it is more than 30 wt. %, the pore size is too large to be suitable.

Cosmetic Composition

The scoria impregnated powder according to the present invention can be suitably applied to a cosmetic composition. In this case, the cosmetic composition preferably includes 2 to 80% by weight of the scoria impregnated powder based on the total weight of the composition. If the content is less than 2% by weight, there arises a problem that the oil absorption property is lowered, and if it exceeds 80% by weight, there arises a problem that it affects the stability of the formulation and thus the stability is lowered.

In addition, the cosmetic composition containing the scoria impregnated powder according to the present invention may contain an adjuvant commonly used in cosmetics or dermatology, such as fatty substances, organic solvent, solubilizers, thickeners, gelling agents, softener, antioxidants, suspending agents, stabilizers, foaming agents, fragrances, surfactants, water, ionic or nonionic emulsifiers, fillers, metal ion sequestrants, chelating agents, preservatives, vitamin, blocking agents, wetting agents, essential oil, dyes, pigments, hydrophilic or lipophilic active agents, lipid vesicles or any other ingredient commonly used in cosmetics. Such an adjuvant is introduced in an amount commonly used in the cosmetics or dermatological fields.

The cosmetic composition containing the scoria impregnated powder according to the present invention may be formulated by incorporating a cosmetically or dermatologically acceptable medium or base. The formulations are any formulations suitable for topical application, and for example, can be used in the form of solutions, gels, solids, paste anhydrides, emulsions obtained by dispersing the oil phase in water, suspensions, microemulsions, microcapsules, microgranules, or ionic (liposomes) and non-ionic follicular dispersants, or in the form of creams, skins, lotions, powders, ointments, sprays, packs or conceal sticks. These compositions may be prepared according to conventional methods in the art.

For example, the cosmetic composition may be formulated in the form of any one of a skin, a lotion, a cream, a serum, an emulsion, an essence, a powder, a foundation, and a spray, and more preferably into a mask pack, a sheet pack, a sleep pack, a wash-off pack, a peel-off pack, and the like, but is not particularly limited in formulation, and can be appropriately selected and changed according to the purpose.

Hereinafter, the present invention will be described in more detail by means of examples and drawings. However, it will be apparent to those skilled in the art that the present invention is not limited by the following examples, and various changes and modifications may be made within the spirit and scope of the invention.

In order to prepare the scoria impregnated powder of the present invention, the following composition of Table 1 is prepared.

TABLE 1

| | |
|---|---|
| Scoria powder | Prepared by Bioland, Jeju scoria |
| Poly-(methyl methacrylate)(PMMA) | Prepared by LG PMMA |
| Dichloromethane anhydrous (DCM) | Prepared by Sigma-Aldrich, Purity >99.8% |
| Hexanol(1-hexanol) | Prepared by Sigma-Aldrich, Purity >99% |

Example 1

Spray Drying 1) 40 g of PMMA was dissolved in 1 L of solvent (DCM:Hexanol=9:1, wt %).

2) 40 g of scoria powder was added to the PMMA solution and dispersed using a homogenizer.

3) The scoria powder dispersed PMMA solution was spray-dried under the conditions shown in Table 2 below.

TABLE 2

| | |
|---|---|
| Internal humidity | 30% or more |
| Internal temperature | Maintenance at room temperature |
| Internal pressure | 20 atm. |
| Feed rate | 20% |
| Aspirator | 70% |

4) The scoria powder dispersed PMMA solution was continuously stirred through a stirrer during spray drying.

5) The spray-dried scoria powder/PMMA composite powder particles were thoroughly washed, and then freeze-dried to remove residual solvent completely.

Example 2

Electro-Spraying 1) 40 g of PMMA was dissolved in 10 mL of solvent (DCM:Hexanol=9:1, wt. %).

2) 0.4 g of scoria powder to the PMMA solution was added and the dispersed using a sonicator.

3) The scoria powder dispersed PMMA solution was electro-sprayed under the conditions shown in Table 3 below.

TABLE 3

| | |
|---|---|
| Internal humidity | 30% or more |
| Internal temperature | Maintenance at room temperature |
| Distance | 15 cm |
| Feed rate | 0.01 mL/min |
| Voltage | 10 kV |

4) The spray-dried scoria powder/PMMA composite powder particles were thoroughly washed, and then freeze-dried to remove residual solvent completely.

The scoria impregnated powder, which will be described later, was prepared according to the spray drying method of Example 1 and used in the experiment.

Experimental Example 1

Scanning Electron Microscope (SEM) Image

Figure 1:
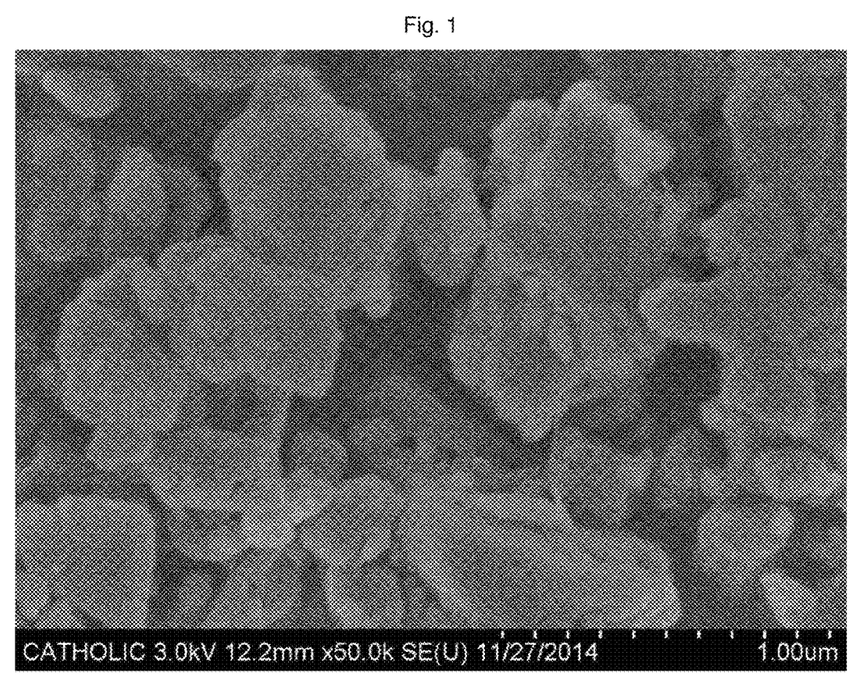
FIG. 1 is a scanning electron microscope (SEM) image of the scoria powder applied to the present invention.
Figure 2:
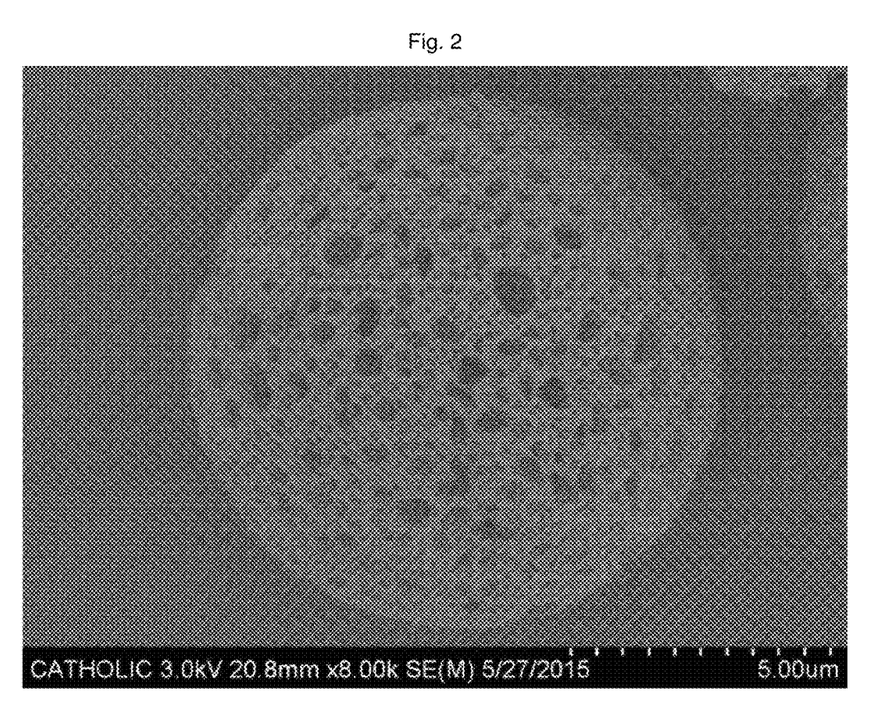
FIG. 2 is a scanning electron microscope (SEM) image of the scoria impregnated powder (scoria sphere) sphere of the present invention.
Figure 3:
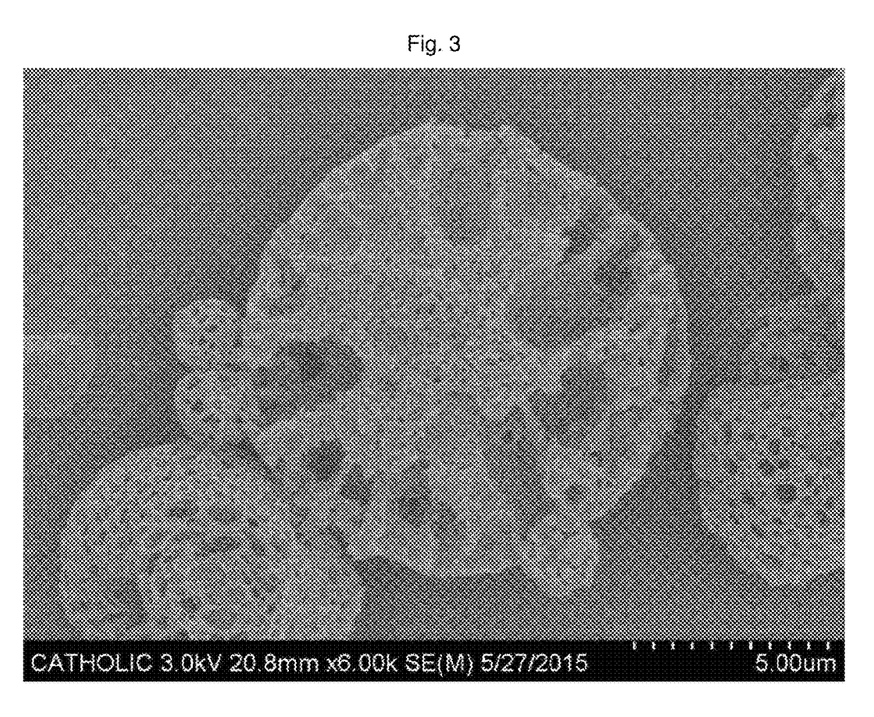
FIG. 3 is a scanning electron microscope (SEM) image of the cross section of the scoria impregnated powder (scoria sphere) of the present invention.

FIG. 1 is a scanning electron microscope (SEM) image of the scoria powder, and FIG. 2 is a scanning electron microscope (SEM) image of the scoria impregnated powder sphere and its cross section which is prepared by uniformly impregnating the scoria powder on the surface and inside of the porous polymer of the poly-(methyl methacrylate) (PMMA) particle. As shown in FIG. 1, it is possible to uniformly impregnate the surface and inside of poly-(methyl methacrylate) (PMMA) particles by introducing the scoria powder by spray drying or electro-spraying, which is a particle of amorphous coarse structure with no porosity, as in FIG. 2 and FIG. 3.

Experimental Example 2

Energy Dispersive X-Ray (EDX) Analysis

Figure 4:
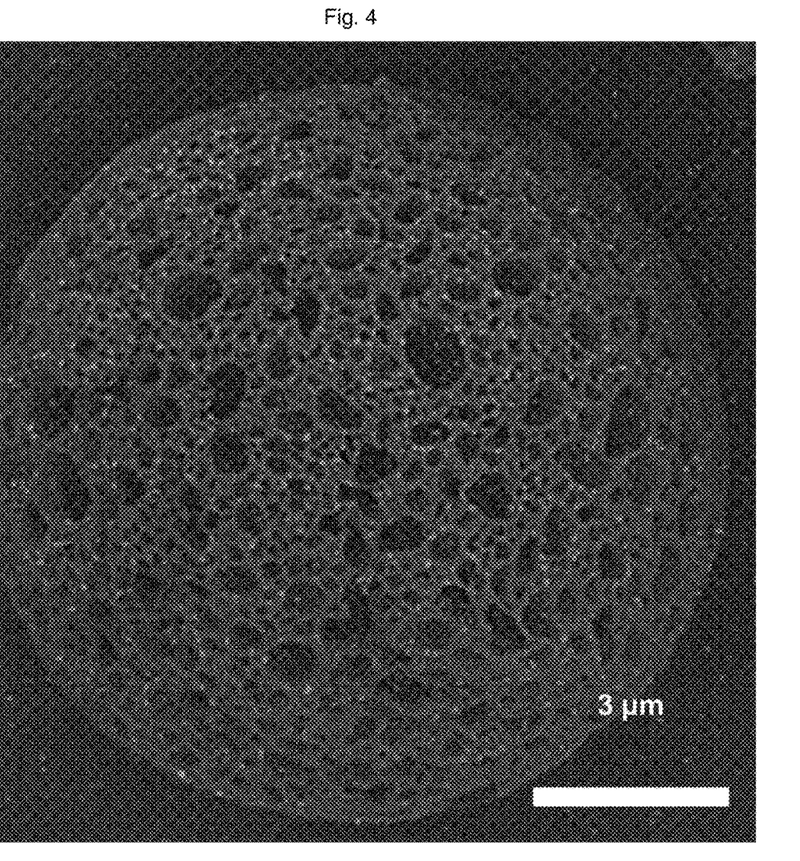
FIG. 4 is an image obtained by quantitatively and qualitatively analyzing each element contained in the scoria impregnated powder (scoria sphere) of the present invention using an energy dispersive X-ray (EDX) analyzer.

FIG. 4 is an image obtained by quantitatively and qualitatively analyzing each element contained in the scoria impregnated powder of the present invention using an energy dispersive X-ray (EDX) analyzer, wherein distribution of silicon (Si), iron (Fe), and aluminum (Al) elements which are the main components of scoria applied in the example of the present invention can be confirmed, and from this, it can be confirmed that the scoria powder was uniformly impregnated and distributed throughout poly-(methyl methacrylate) (PMMA).

Experimental Example 3

Oil Absorption Volume Test 1 g of scoria impregnated powder was weighed using a balance and petri dish, and then the oil absorption volume was measured until the scoria impregnated powder was moistly wetted by dropping the triglyceride oil having similar properties to the sebum of the human body using a pipette. At this time, mixing was performed using a spatula to ensure that the oil was well wetted.

Figure 5:
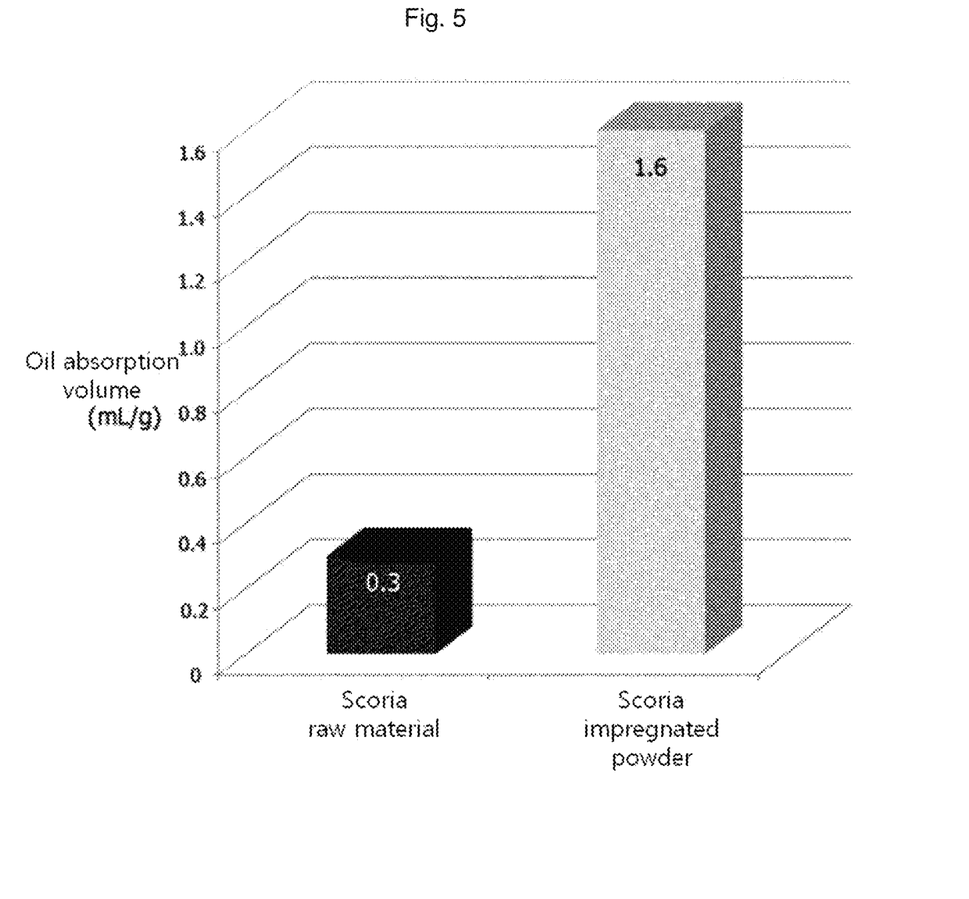
FIG. 5 is the test results on the oil absorption volume (mL/g) of the scoria impregnated powder (scoria sphere) of the present invention.

As shown in FIG. 5, it can be confirmed that the oil absorption volume of scoria impregnated powder is 1.6 mL/g, which is more than 5 times the oil absorption volume of scoria raw powder of 0.3 mL/g. This effect is caused by maintaining the large pore size and the high porosity although the scoria impregnated powder of the present invention contains 50% by weight of the scoria powder.

The invention claimed is:

1. A composite powder in which a porous polymer is impregnated with scoria powder particles, wherein the average particle diameter of the scoria powder is 0.1 to 2 μm.

2. The composite powder according to claim 1, wherein the scoria powder is impregnated in an amount of 50 to 90% by weight based on the total weight of the composite powder.

3. The composite powder according to claim 1, wherein the porous polymer comprises at least one selected from the group consisting of poly-(methyl methacrylate), poly-(vinyl pyrrolidone), poly-(caprolactone), poly-(L-lactic acid), poly-(ethylene oxide), poly-(propylene oxide), poly-(dimethyl siloxane), poly-(lactic-co-glycolic acid), polystyrene and a copolymer thereof.

4. The composite powder according to claim 1, wherein the composite powder has the average particle diameter of 5 to 20 in and is a sphere.

5. The composite powder according to claim 1, wherein the porosity of the composite powder is 40 to 85%.

6. The composite powder according to claim 1, wherein the average pore size of the composite powder is 15 to 800 nm.

7. A method for preparing a composite powder in which a porous polymer is impregnated with scoria powder particles, comprising:
spray drying or electro-spraying a dispersion in which the scoria powder is dispersed in the polymer solution to prepare the composite powder,
wherein the average particle diameter of the scoria powder is 0.1 to 2 μm.

8. The method according to claim 7, wherein the solvent of the polymer solution is a mixed solvent of dichloromethane and hexanol.

9. The method according to claim 8, wherein the weight ratio of dichloromethane to hexanol is 9:1 to 7:3.

10. A cosmetic composition containing the composite powder according to claim 1.

* * * * *